United States Patent [19]

Carcasona et al.

[11] Patent Number: 5,710,260

[45] Date of Patent: Jan. 20, 1998

[54] METHOD OF EXTRACTING SENNOSIDES A, B AND A1

[75] Inventors: Alfons Carcasona, Köln; Wolf Grimminger, Bergisch-Gladbach, both of Germany; Pentti Hietala, Helsinki, Finland; Helga Zaeske; Klaus Witthohn, both of Overath, Germany

[73] Assignee: Madaus AG, Cologne, Germany

[21] Appl. No.: 614,772

[22] Filed: Dec. 21, 1995

Related U.S. Application Data

[63] Continuation of Ser. No. 342,660, Nov. 21, 1994, abandoned, which is a continuation of Ser. No. 219,005, Mar. 28, 1994, abandoned, which is a continuation of Ser. No. 969,253, filed as PCT/EP92/01428, Jun. 24, 1992, abandoned.

[30] Foreign Application Priority Data

Jun. 25, 1991 [DE] Germany ............ 41 20 991.5

[51] Int. Cl.$^6$ .................. C07H 15/244; C07H 1/00; A61K 35/78
[52] U.S. Cl. .................. 536/18.5; 424/195.1; 514/783; 536/124; 536/127; 536/128
[58] Field of Search .................. 424/195.1; 514/783; 536/18.5, 124, 127, 128

[56] References Cited

U.S. PATENT DOCUMENTS

| | | | |
|---|---|---|---|
| 4,256,875 | 3/1981 | Gabriel et al. | 536/4 |
| 4,402,944 | 9/1983 | Callahan et al. | 424/180 |
| 4,511,561 | 4/1985 | Madaus et al. | 424/195.1 |
| 4,595,592 | 6/1986 | Hietala | 424/195.1 |
| 5,232,699 | 8/1993 | Colliopoulos | 424/195.1 |
| 5,234,916 | 8/1993 | Hord | 514/57 |
| 5,391,775 | 2/1995 | Carcasona et al. | 552/262 |
| 5,393,898 | 2/1995 | Carcasona et al. | 552/262 |

FOREIGN PATENT DOCUMENTS

| | | |
|---|---|---|
| 540082 | 4/1957 | Canada . |
| 540737 | 5/1957 | Canada . |
| 2594337 | 2/1986 | France . |
| 3200131 | 7/1983 | Germany . |
| 031146 | 3/1981 | Japan . |
| 62-178598 | 8/1987 | Japan . |
| 555450 | 8/1943 | United Kingdom . |
| 1135528 | 12/1968 | United Kingdom . |
| 2018588 | 10/1979 | United Kingdom . |

OTHER PUBLICATIONS

Leng—Peschlow, E. *J. Pharm. Pharmacol.*, vol. 32(5), pp. 330–35, (1980). [Abstract Only].

Kobashi, Kyoichi et al. *Chem. Pharm. Bull.*, 35(5), pp. 1998–2003, (1987).

*Primary Examiner*—John Kight
*Assistant Examiner*—Howard C. Lee
*Attorney, Agent, or Firm*—Felfe & Lynch

[57] ABSTRACT

Sennosides A, B and A1 of the formula:

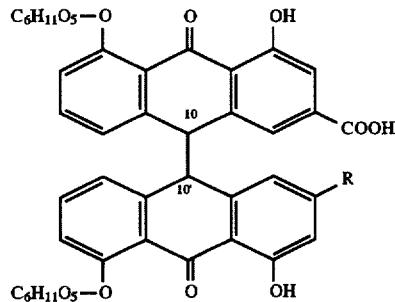

which are substantially free from sennosides C, D and D1, and from aloe-emodin derivatives, are prepared by a process wherein a) a sennoside mixture is reduced to rhein-9-anthrone-8-glucoside and aloe-emodin-9-anthrone-8-glucoside, b) a liquid-liquid partitioning of the compounds obtained is carried out between a polar organic solvent which is only partly miscible with water and an aqueous phase and c) the rhein-9-anthrone-8-glycosides contained after the partitioning in the aqueous phase is again oxidized to the corresponding sennosides and these are recovered.

15 Claims, No Drawings

METHOD OF EXTRACTING SENNOSIDES A, B AND A1

This application is a continuation of application Ser. No. 08/342,660, filed Nov. 21, 1994, now abandoned which is a continuation of U.S. Ser. No. 08/219,005 filed Mar. 28, 1994, now abandoned, which is a continuation of U.S. Ser. No. 07/969,253, filed as PCT/EP92/01428 Jun. 24, 1992, now abandoned.

The present invention is concerned with a process for obtaining sennosides A, B and A1 which are substantially free from sennosides C, D and D1 and from aloe-emodin components, as well as with the sennosides obtainable according to this process and pharmaceutical compositions which contain these sennosides.

The sennosides are laxative-acting substances which occur in the dried drugs of the genus Cassia and Rheum. The senna drug consists of the dried leaves and pods of the senna plant, for example of Indian senna (*Cassia angustifolia*).

The laxative-active sennosides are dianthrone glucosides derived from rhein and aloe-emodin, the most important ones being sennosides A, B, A1, C, D and D1. They correspond to the general formula:

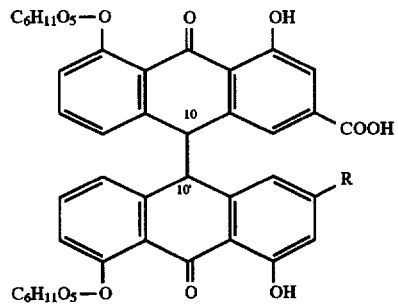

In the case of sennosides A, B and A1, R stands for COOH and in the case of sennosides C, D and D1, R stands for CH$_2$OH. Sennosides A, B and A1 and C, D and D1 are stereoisomers and differ from one another by the configuration on carbon atoms 10 and 10'.

Besides the sennosides, the crude drug also contains aglycones (sennidines), semi-glycosylated sennidines, polymers, decomposition products of the sennosides, aloe-emodin and derivatives thereof etc. which can bring about undesired side affects, such as ill-feeling, vomiting, flatulence and colic.

Processes for obtaining sennosides from senna drug are described, for example in DE-B-16 17 667, FR-M 6611, GB-A-832017 and DE-A-3 200 131. Depending upon the drug, the sennosides obtained according to these known processes contain a sennoside mixture with 1.5 to 5% of sennosides C, D and D1. As has already been indicated above, these contain in their molecule a moiety derived from aloe-emodin of the formula:

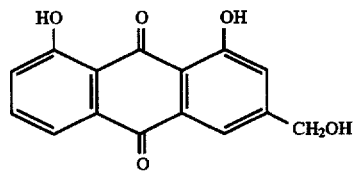

It would be desirable if sennosides could be obtained which are substantially free from sennosides C, D and D1.

A substantially complete separation of sennosides C, D and D1 from a sennoside mixture is not known from the present state of the art.

Therefore, it is an object of the present invention to provide a process for obtaining sennosides A, B and A1 which are substantially free from undesired accompanying materials and especially from sennosides C, D and D1.

Thus, according to the present invention, there is provided a process for obtaining sennosides A, B and A1 of the formula:

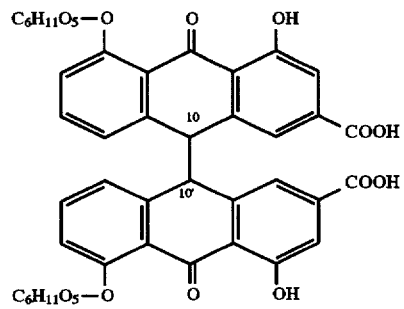

wherein
a) a sennoside mixture is reduced to rhein-9-anthrone-8 glucoside and aloe-emodin-9-anthrone-8-glucoside,
b) a liquid-liquid partitioning of the compounds obtained is carried out between a polar organic solvent which is only partly miscible with water and an aqueous phase and
c) the rhein-9-anthrone-8-glucoside contained after partitioning in the aqueous phase is again oxidised to the corresponding sennosides and these are recovered.

Step a)

As starting material for the process according to the present invention, there are, in general, used sennoside mixtures such as are obtained in the extraction of senna drug according to the above-mentioned processes. For example, as starting material, a sennoside mixture can be used which is obtained by the process described in DE-A-32 00 131. Thereafter, the senna drug is first extracted with aqueous methanol. The concentrate remaining after complete removal of the methanol contains the sennosides in the form of the potassium salts. This concentrate can be used as starting material for the process according to the present invention.

The concentrate can also be purified by liquid—liquid extraction with alcohols or ketones which are partly soluble in water, for example butan-2-ol, butan-2-one or acetone. The raffinate is acidified to a pH of about 1.5 to 2.0 and the sennosides are brought to crystallisation by seeding. The crude sennoside mixture obtained can also be used as starting material for the process according to the present invention. If desired, the crude sennoside mixture can also be recrystallized.

Alternatively, the concentrate mixed with an alcohol or ketone which is partly soluble in water, especially butan-2-ol, can be used as starting material.

In the case of the extraction of the senna drug, the ratio of drug to extraction solvent is preferably 1:4 to 1:15 and especially 1:4 to 1:10.

The extraction is preferably carried out in the presence of a buffer, for example trisodium citrate, glycine, sodium bicarbonate or saccharose.

According to the process of the present invention, these starting materials are completely reduced to the corresponding rhein-9-anthrone-8-glucoside (R=COOH) and to the corresponding aloe-emodin-9-anthrone-8-glucoside (R=CH$_2$OH) of the general formula:

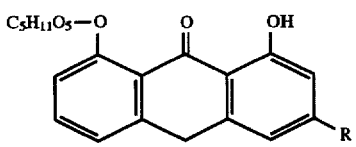

Reducing agents with an appropriate reduction potential include, for example, stannous chloride, sulphur dioxide, alkali metal boron hydrides and preferably alkali metal dithionites, especially sodium dithionite.

For carrying out the reduction, the starting material can be present in aqueous solution or suspension and the reducing agent added thereto in solid form or dissolved in water. Especially in the case of using senna fruit primary extract according to DE-A-32 00 131 (aqueous concentrate), it is also possible to work in a two-phase mixture by adding a polar organic solvent which is partly miscible with water, especially butan-2-ol or acetone.

The reduction can be carried out at ambient temperature or at an elevated temperature. The reduction is preferably carried out at 40° to 60° C. and especially at 50° to 55° C. Working can be carried out at a weakly acidic to weakly alkaline pH value of the solution or suspension of the starting sennoside solution and preferably at a PH value of from 5 to 10.5. If desired, the reduction can be carried out several times, especially 2 to 10 times.

The 9-anthrone-8-glucoside formed is precipitated out by the addition of an acid, for example of sulphuric acid, up to a pH value of about 2 to 4.5. The temperature should thereby preferably be not more than 40° C. In the case of precipitating out the anthrone glucosides, and in the case of of the isolation thereof, for example by filtration, it is preferable to work under an atmosphere of nitrogen in order to prevent an uncontrolled oxidation of these compounds.

It is important that the reduction proceeds to completion. Therefore, it is preferable to use the reducing agent in large excess. Dithionites and especially sodium dithionite are, in general, used in a 1 to 4 fold amount by weight, referred to the content of sennosides in the starting material. Furthermore, the reducing agent is allowed to act for at least 2 hours and preferably for at least 3 hours. In general, the reduction takes place for not longer than 10 hours. A post-reduction is preferably carried out under the given conditions.

Before its use in step b), the product obtained is preferably reprecipitated by bringing it into aqueous solution by the addition of a base, for example sodium hydroxide or potassium hydroxide, to a pH value of about 6 to 7, extracting the solution with butan-2-ol, butan-2-one or acetone and again precipitating out the product by the addition of an acid to a pH value of about 2 to 4.

Step b)

In this step, the aloe-emodin components and especially aloe-emodin-9-anthrone-8-glucoside are removed. For this purpose, a liquid-liquid partitioning of the product obtained is carried out in a polar organic solvent which is only partly miscible with water and an aqueous phase. Appropriate polar organic solvents include $C_4$–$C_5$-alkanols and di-$C_1$–$C_3$-alkyl ketones, for example butan-1-ol, butan-2-ol, butan-2-one and acetone, butan-2-ol and acetone preferably being used.

To the aqueous phase is preferably added a reducing agent in order to impart to the aqueous phase during the whole of the liquid-liquid partitioning a redox potential of −210 mV or more negative. It is preferred to use the same reducing agent as in step a). In the case of using an alkali metal dithionite as reducing agent, in general a 2 to 4% by weight solution at a pH value of 7 to 10.5 is sufficient in order to maintain the mentioned potential conditions. The pH value is preferably maintained in this range by the addition of a buffer.

The volume ratio of aqueous phase (heavy phase) to organic phase (light phase) is generally in the range of from 1:5 to 1:40.

The liquid-liquid extraction preferably takes place in countercurrent. The mixture of the anthrone compounds is thereby introduced in the form of the solution obtained after the reduction or, when the anthrone compounds have been isolated, in the form of a 3 to 15% by weight solution.

After the partitioning, the desired rhein-9-anthrone-8-glucoside is present in the aqueous phase. It is precipitated out by the addition of an acid up to a pH value of about 2 to 4 and recovered in the usual way.

Step c)

In this step, the rhein-9-anthrone-8-glucoside is again oxidised to the corresponding sennoside compounds. Oxidation agents appropriate for this purpose include hydrogen peroxide, manganese dioxide, permanganates and manganic acetonylacetonate. However, the oxidation is preferably carried out with oxygen. As the source of oxygen, air can, for example, be used.

Since rhein-9-anthrone-8-glucoside is insoluble in water, for the oxidation it is converted into a soluble form. This can take place, for example, by converting it into an alkali metal salt or into the calcium salt by the addition of an appropriate base up to a pH value of about 6 to 7. If desired, a small amount (up to about 30% by volume) of a solvent which is only partly miscible with water, especially butan-2-ol, can be added to the solution.

The oxidation is carried out in a solution which is as concentrated as possible because, in this way, the formation of the desired sennosides is favoured. The oxidation is preferably carried out with a solution which contains about 250 to 300 g of rhein-9-anthrone-8-glucoside per liter of solvent. In the case of using oxygen as oxidation agent, this is preferably passed through the solution.

The oxidation with oxygen can be facilitated by the use of a catalyst. Appropriate catalysts include, for example, palladium black and ferric salts, especially ferric chloride. In general, the amount of catalyst lies in the range of 0.2 to 2% by weight, referred to the amount of rhein-9-anthrone-8-glucoside, and especially in the range of 0.5 to 1% by weight.

Alternatively, the oxidation can be carried out with a ferric salt, for example ferric sulphate or ferric chloride, at a pH value of 8 to 8.5. It is thereby preferred to work at 30° to 50° C. and in the presence of trisodium citrate.

The oxidation is carried out until the rhein-9-anthrone-8-glucoside can no longer be detected (absence of the ultraviolet fluorescence of the anthrone compounds).

The sennosides are obtained in the usual way by acidification of the solution obtained. The solution is preferably diluted before the addition of the acid with the solvent used, for example water/butan-2-ol, to 2 to 3 times the volume present. In this way, it is achieved that the rhein-8-glucoside formed as by-product remains substantially in solution in the case of the precipitation of the sennosides.

The separation of the rhein-8-glucoside can also take place via the calcium salt because the calcium salt of rhein-8-glucoside is insoluble and precipitates out, whereas the calcium salts of the sennosides remain in solution.

The sennosides are precipitated out by the addition of an acid to a pH of about 2 to 4 and then recovered in the usual way.

The sennosides obtained are substantially the sennosides A, B and A1. They are substantially free from sennosides C, D and D1 and from other aloe-emodin contaminations. The contents of sennosides C, D and D1 in the product obtained according to the present invention is less than 100 ppm, determined according to the methods of analysis described in the following Examples.

The present invention is also concerned with the mixture of sennosides A, B and A1 obtainable according to the present invention, as well as with pharmaceutical compositions which contain the said mixture.

The field of use, the dosage to be administered and the appropriate forms of dosage are known from and described in the initially mentioned publications.

The following Examples are given for the purpose of illustrating the present invention:

EXAMPLE 1

Obtaining the sennoside mixture used as starting material.

In each case, 40 kg of senna drug are in introduced into two percolators, connected in series, with a volume of 250 liters and covered with a perforated steel plate. 70% methanol is used as solvent for the extraction which is passed to the drug in the first percolator. The solution formed in the first percolator is passed to the drug which is present in the second percolator. The solvent is thereby allowed to flow freely through the first percolator.

For the extraction of 40 kg of senna drug, there is used, in all, 160 liters of methanol. After this volume of 70% methanol has passed through the two percolators and the corresponding amount of percolate has been collected, the emptying pipe of the percolator is coupled with a post-percolate container and then 60 liters of 70% methanol are passed through the percolators. Thereafter, the remaining free solvent is passed from the first percolator into the upper part of the second percolator and the post-percolate is collected until it makes up a total of 120 liters. The first percolator is then emptied and again filled with 40 kg of senna drug and the post-percolate is pumped on to the drug, 120 liters of post-percolate thereby sufficing in order to cover the drug in the percolator. Subsequently, the temperature of the solution is brought to +30° C. Thereafter, it is left to stand overnight. This percolator is connected with the one which has been previously extracted and the extraction is carried out as described above.

In each case, for 40 kg of drug there are collected 160 liters of percolate from which the methanol is removed in a vacuum rotary evaporator which is equipped with a packed column. About 50 liters of bottom product are obtained. This concentrate is extracted with an equal volume of butan-2-ol which is saturated with water. The phases are then separated and the aqueous phase is further worked up.

Step a
Reduction of the sennosides to rhein-9-anthrone-8-glucosides 1.0 liter of the extracted concentrate is brought to pH 7.5 with a 48% aqueous solution of sodium hydroxide. It is heated to 60° C. and, while stirring, 90 g of sodium dithionite in solid form are added to the solution over the course of half an hour. After completion of the addition, stirring is continued for a further hour. Subsequently, while stirring, concentrated sulphuric acid is added thereto until the pH value is 2. Cooling to ambient temperature is carried out over the course of 2 hours and the precipitated crystalline material is filtered off and washed with sulphur dioxide-containing water.

If desired, crude rhein-9-anthrone-8-glucoside is reprecipitated. The still moist filter cake is dissolved in a mixture of 15 parts by volume of butan-2-ol and 85 parts by volume of water which contains 0.5% by weight of sodium pyrosulphite in such a manner that, by the addition of a 48% aqueous solution of sodium hydroxide up to a pH value of 7, a 10% solution (w/v) is obtained. The solution is acidified with concentrated hydrochloric acid to a pH value of 2.8 or below and left to stand for 2 hours. The precipitate obtained is filtered off, washed with water containing sulphur dioxide or sodium pyrosulphite and dried. The yield is 90%.

A renewed reduction (post-reduction) is carried out in the following way with the product obtained in this manner: 3.0 g of the crude, dried rhein-9-anthrone-8-glucoside or the corresponding amount of the moist product are dissolved in 15 ml of water, together with 1.4 g of sodium dithionite and 2.3 ml 5N aqueous sodium hydroxide solution. Subsequently, it is made up with water to 24 ml and the solution is heated for 20 minutes at 55° C. Thereafter, a further 1.5 g of sodium dithionite is added to the solution, followed by heating to 55° C. for 20 minutes. 0.9 ml of 5N aqueous sodium hydroxide solution and 1.5 g of sodium dithionite are then added thereto. After heating for 20 minutes to 55° C., a further 0.9 ml of 5N aqueous sodium hydroxide solution are again added thereto. The solution obtained is then introduced directly into the following liquid-liquid extraction.

Step b)
Separating off of the aloe-emodin components

The separating off of the aloe-emodin components takes place by liquid-liquid partitioning of the 9-anthrone-8-glucosides in countercurrent with an apparatus of 60 mixer-settler units. As aqueous, heavier phase, there is used a solution of 3.0 g. sodium dithionite in 3.5 ml 5N aqueous sodium hydroxide solution and 96 ml of water. As organic, lighter phase, there is used water-saturated butan-2-ol or acetone. The two phase are supplied to the apparatus in such a manner that the volume ratio of the heavier phase to the lighter phase is 1:10.

The mixture to be separated is supplied to the apparatus in the form of the freshly reduced solution or in the form of a solution of appropriate pH value and of appropriate concentration which contains the 9-anthrone-8-glucosides obtained from step a) in such a manner that 30 parts by volume of the organic phase are used per one part by volume of mixture to be separated.

The pH of the solution containing the mixture is maintained at 9 to 9.5 with the help of a glycine buffer. The buffer of 3 parts by volume of a 7.5% glycine solution and 1 part by volume of 1N aqueous sodium hydroxide solution is introduced in an amount of 240 ml of buffer solution per 150 g of crude rhein-9-anthrone-8-glucoside. The undesired aloe-emodin compounds enrich in the organic phase, whereas the rhein-9-anthrone-8-glucoside remains in the aqueous phase. The aqueous phase is acidified with sulphuric acid to pH 2.8, the precipitate formed is filtered off and washed with water and acetone and dried in the air at ambient temperature. In this way, there is obtained rhein-9-anthrone-8-glucoside with a content of aloe-emodin components of 49 ppm (determined as aloe-emodin); yield 97%, referred to rhein-9-anthrone-8-glucoside.

Step c)
Oxidation of the rhein-9-anthrone-8-glucosides 18.8 g of the rhein-9-anthrone-8-glucoside obtained are dissolved in 56 ml of water and 11 ml of butan-2-ol, 17N aqueous sodium hydroxide solution being added thereto until the pH is 6.5. While stirring, air is blown through this solution for 5 hours in a cylindrical vessel with the help of a glass frit, the rate of flow of the air being 40 ml/minute. The course of the oxidation is monitored by means of HPLC.

When rhein-9-anthrone-8-glucoside can no longer be detected, the solution is diluted to about 200 ml with water/butanol (65:11 v/v). Concentrated hydrochloric acid is added thereto until the pH is 1.5 to 2, followed by stirring for 2 hours at ambient temperature. The precipitated crystals are filtered off, washed with water and acetone and dried. There are obtained 14.4 g (76% of theory) of pure sennoside mixture with a content of 41 ppm aloe-emodin components (determined as aloe-emodin), according to the analysis procedure described for step c) in Example 2.

EXAMPLE 2

The process is as described in Example 1 but the oxidation in step c) is carried out as follows:

150 g of the pure rhein-9-anthrone-8-glucosides and 0.75 g ferric chloride hexahydrate are dissolved in 480 ml of water and 120 ml of butan-2-ol. A 48% aqueous solution of sodium hydroxide is added thereto until a pH value of 6.5 is reached and the rhein-9-anthrone-8-glucoside has dissolved. The solution is introduced into a vessel with a sinter bottom plate. Subsequently, a vigorous current of air is passed through the solution. The oxidation is finished after about 30 minutes. The solution is subsequently diluted with a mixture of 120 ml butan-2-ol and 480 ml of water. 7.5 g sodium dithionite are added thereto and the pH value of the solution is adjusted to 2.0 by the addition of concentrated hydrochloric acid. The solution is stirred for 18 hours. Subsequently, the precipitate obtained is filtered off, washed with 600 ml of water and 800 ml of acetone and dried. The content of anthranoid compounds in the product obtained is from 94 to 95%.

The product is taken up in 200 ml of butan-2-ol and precipitated with 800 ml of water with the addition of 5.5 g sodium pyrosulphite. After filtering off and drying the precipitate obtained, there are obtained 95.4 g of a product of anthanoid compounds of the following composition (according to HPLC, analysis of a typical experiment):

| | |
|---|---|
| rhein-8-glucoside | 1.5% |
| sennoside B | 49.7% |
| sennoside A1 | 13.3% |
| sennoside A | 33.6% |
| sennidine monoglucosides | 1.1% |
| rhein | 0.02% |
| | 99.22% |

Sennosides C and D and aloe-emodin glucoside could not be detected by HPLC. The total content of aloe-emodin and of the derivatives thereof was determined as being 30 ppm according to the following method:

Sennosides C and D and aloe-emodin-8-glucoside can no longer be dependably determined as sennosides in the ppm range by means of HPLC chromatography. Therefore, it is necessary to convert the substance to be investigated by oxidation with ferric chloride and simultaneous hydrolysis with hydrochloric acid in a two-phase mixture of aqueous solution/carbon tetrachloride into rhein or aloe-emodin. The rhein is then converted into a salt so that it can be extracted into the aqueous phase and the aloe-emodin in the organic phase can be determined by means of HPLC. In this way, there can be given the total content of sennosides C and D, aloe-emodin-8-glucosides and other aloe-emodin components, expressed as aloe-emodin.

EXAMPLE 3

The extraction of the senna drug and the reduction of the sennosides described in Example 1 is repeated. The subsequent reduction is then carried out as follows:

14.0 g saccharose, 4.5 g 85% sodium dithionite and 13.3 g potassium acetate are dissolved in 133 ml of water and 1.3 ml of 48% sodium hydroxide solution and 17.3 g potassium carbonate are added thereto. Subsequently, the reaction mixture is mixed with 293 ml acetone and 50 ml of water. The mixture is shaken in a separating funnel and the phases are separated, 375 ml of upper phase (acetone phase) and 130 ml of lower phase thereby being obtained.

1.4 ml of a 48% sodium hydroxide solution and 10 g of crude rhein-9-anthrone-8-glucoside are dissolved in 98 ml of the lower phase. The solution is warmed to 45° to 50° C. and maintained at this temperature for 20 to 30 minutes. Subsequently, 1.0 ml of a 48% sodium hydroxide solution and 3.4 g sodium dithionite are added thereto and heated for a further 20 to 30 minutes to 45° to 50° C. Subsequently, there are again added 1.0 ml of 48% sodium hydroxide solution and 3.4 g sodium dithionite, followed by heating for 20 to 30 minutes to 45° to 50° C.

The separation of the aloe-emodin components takes place by liquid-liquid partitioning of the reduced solution in countercurrent against the above-mentioned upper phase (acetone phase). The raffinate phase flowing off and containing the rhein-9-anthrone-8-glucoside is concentrated to 400 ml and mixed with 20 ml butan-2-ol. Hydrochloric acid or sulphuric acid is added thereto up to a pH value of 4.0 to 4.2. The precipitate formed is filtered off, washed with 40 ml of water and 30 ml of acetone and subsequently dried. The subsequent oxidation takes place in the manner described in Example 2.

EXAMPLE 4

The concentrate obtained after extraction of the senna drug is mixed with about 2 liters of butan-2-ol. The reduction of the mixture of the senna fruit concentrate and butan-2-ol is then carried out in 7 steps under nitrogen as protective gas. After reduction step I, there follows the precipitation of the crude rhein-9-anthrone-8-glucoside.

Reduction step I 100 liters of a mixture of senna fruit concentrate and butan-2-ol containing about 4 kg of sennosides are placed in a stirrer container and covered with nitrogen. While stirring, 6 liters of a 20% by weight aqueous solution of sodium hydroxide and thereafter 350 liters of water-saturated butan-2-ol, for example from step II, are added thereto and stirred for 15 minutes. The batch is heated to 42° to 50° C., mixed with 7 kg sodium dithionite mud further stirred for 45 minutes. The pH value is maintained at 7.5 to 8 with 20% by weight aqueous sodium hydroxide solution. The reduction potential (against au Ag/AgCl electrode) is, if necessary, maintained below −630 mV by the addition of sodium dithionite. After cooling to 30° to 35° C., precipitation is carried out within 1.5 hours with 10% by weight sulphuric acid to pH <4. The resultant suspension is stirred for about 10 hours at <25° C. with a slow speed of stirring and the resultant precipitate is filtered off. The precipitate is suspended in 60 liters of 15% by weight butan-2-ol, stirred for 30 minutes at 50° to 60° C. and subsequently filtered. The residue is washed with 100 liters of demineralised water. The crude yield of rhein-9-anthrone-8-glucoside is more than 82%, referred to the sennosides used.

Reduction step II 3.3 kg crude rhein-9-anthrone-8-glucoside from step I are suspended in a mixture of 42 liters of demineralised water and 7.4 liters butan-2-ol. The suspension is brought into solution with 2 liters of 20% by weight aqueous sodium hydroxide solution and 9.9 kg trisodium citrate and thereafter mixed with 3.3 kg sodium dithionite and 350 liters water-saturated butan-2-ol, for example from step III. The batch is heated to 42° to 45° C., the pH value being maintained at 8.5 to 9 with 20% by weight aqueous sodium hydroxide solution. The reduction potential (against an Ag/AgCl electrode) is, if necessary, maintained below −750 mV by the addition of sodium dithionite. After standing for 30 minutes, the upper phase is removed and the lower phase further worked up in step III.

Reduction step III

The reduction/extraction process described in step II is repeated with the lower phase from step II, with the addition of the following chemicals:

1.65 kg sodium dithionite, 0.8 liters 20% by weight aqueous sodium hydroxide solution and 350 liters water-saturated butan-2-ol, for example from step IV.

Reduction steps IV and VII

The reduction/extraction process described in step II is repeated with, in each case, the lower phase from the preceding step with the addition of the following chemicals:

0.825 kg sodium dithionite 0.4 liters of 20% by weight aqueous sodium hydroxide solution and 350 liters of water-saturated butan-2-ol, for example in each case from the following step—countercurrent principle.

The lower phase separated off in step VII is cooled to 30° to 35° C. and the rhein-9-anthrone-8-glucoside precipitated out as described in step I. The resultant precipitate is filtered off and washed with 100 liters of demineralised water. Subsequently, it is covered with 10 liters of ferric sulphate solution (28 kg ferric sulphate in 100 liters of demineralised water).

The rhein-9-anthrone-8-glucoside is then converted into the sennosides in the manner described in Example 1 or 2.

EXAMPLE 5

The oxidation of rhein-9-anthrone-8-glucoside can also take place according to the following process:

6.0 kg of filter-moist rhein-9-anthrone-8-glucoside are mixed with 12.6 kg trisodium citrate. This mixture is dissolved in 7.0 liters of 1N aqueous sodium hydroxide solution with vigorous stirring and mixed with 0.7 liters of butan-2-ol. Subsequently, it is mixed with 8.8 liters of ferric sulphate solution (28 kg ferric sulphate in 100 liters of demineralised water) and sufficient 20% aqueous sodium hydroxide solution added to give a pH value of about 8.3. The solution is left to react for 3 to 4 hours at about 40° C., then acidified with 52% sulphuric acid to pH value 1.8 to 2.0 and worked up in the manner described in Example 1.

EXAMPLE 6

Alternatively, rhein-9-anthrone-8-glucoside is dissolved in 50 ml of water by the addition of calcium hydroxide-saccharose solution (prepared by suspending 7.0 g calcium-hydroxide in a solution of 30.0 g saccharose in 100 ml of water and removal of the undissolved calcium hydroxide). 20 ml butan-2-ol are added thereto and a vigorous current of air is passed through the solution over the course of 90 minutes. 5.0 g calcium chloride dihydrate are added thereto and the pH value is adjusted to 8.5 with the calcium hydroxide-saccharose solution. The precipitate formed is filtered off and the filtrate is diluted with water to 340 ml, mixed with 60 ml butan-2-ol and adjusted to pH value 2.0 with concentrated hydrochloric acid. Further working up takes place in the manner described in Example 1.

Pharmacological investigations

Laxative action

The laxative effect of the sennoside mixture according to the present invention was determined on mice. Male NMRI mice were used which were kept during the experiment in Plexiglas cages and which received standard feed mixed with tap water (1:1) of mushy consistency. A separate supply of drinking water was not provided during the experiment.

The animals received 100, 200 and 400 mg/kg of the sennoside mixture in 10 ml of 0.5% aqueous sodium hydrogen carbonate/kg by means of a stomach probe. After administration of the compounds to be tested, faeces and urine of the animals were collected over the course of 24 hours and then determined. The results obtained, referred to kg of body weight, are summarised in the following Table.

TABLE

Laxative effect of the sennoside mixture according to the present invention on mice

| dosage (mg/kg) | number of animals | number of normal faecal pellets | number of soft faecal pellets | soft faeces as % of the total faecal excretion |
|---|---|---|---|---|
| 0 | 30 | 1265 | 0 | 0 |
| 100 | 40 | 587 | 144 | 28.0 |
| 200 | 30 | 223 | 239 | 56.0 |
| 400 | 30 | 236 | 282 | 60.0 |

It can be seen that the sennosides display a good laxative action which commences relatively quickly. The time up to the appearance of the first soft faeces (2 hours) is, however, also to be combined with the previous transit to the large intestine and a breakdown of the sennosides by the flora of the large intestine. A dosage-action relationship is present.

Acute toxicity

In each case, male and female Wistar rats were given sennosides once in dosages of from 200 to 25,000 mg/kg by means of a stomach probe.

Macroscopic organ damage caused by the administered substances could not be observed. The following $LD_{50}$ values were ascertained:

| | |
|---|---|
| male rats: | 5200 $-$ 720 mg/kg<br>+ 840 |
| female rats: | 3530 $-$ 340 mg/kg<br>+ 380 |

In the case of male and female mice (n=8, strain NMRI), the maximum administerable dose of 5000 mg/kg did not result in any deaths. In all mice, diarrhoea occurred, although to a lesser extent than in the case of rats. For both sexes, the $LD_{50}$ values were >5000 mg/kg.

We claim:

1. A process for obtaining sennosides A, B and A1 of the formula:

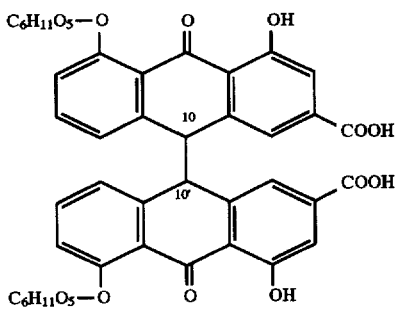

which are substantially free from sennosides C, D and D1 and from aloe-emodin derivatives, wherein a) a sennoside mixture is reduced to rhein-9-anthrone-8-glucoside and aloe-emodin-9-anthrone-8-glucoside, b) a liquid-liquid partitioning of the compounds obtained is carried out between a polar organic solvent which is only partly miscible with water and an aqueous phase and c) the rhein-9-anthrone-8-glucoside contained after partitioning in the aqueous phase is again oxidized to the corresponding sennosides and these are recovered.

2. The process of claim 1, wherein the sennoside mixture is obtained by extraction of senna drug with aqueous methanol.

3. The process of claim 2, wherein the extraction with methanol is carried out in the presence of a buffer.

4. The process of claim 1, wherein an alkali metal dithionite is used as reducing agent in step a).

5. The process of claim 4, wherein the process is performed at a pH value of 5 to 10.5.

6. The process of claim 1, wherein butan-2-ol or acetone is used as polar organic solvent in step b).

7. The process of claim 1, wherein an aqueous phase is used in step b), the redox potential of which is −210 mV or more negative.

8. The process of claim 1, wherein the liquid-liquid partitioning in step b) is carried out in a countercurrent mode.

9. The process of claim 1, wherein the oxidation in step c) is carried out with oxygen or a ferric salt.

10. The process of claim 9, wherein the oxidation with oxygen is carried out at a weakly acidic pH value.

11. The process of claim 10, wherein the oxidation is carried out in the presence of a catalyst.

12. The process of claim 11, wherein the catalyst is a ferric salt.

13. A composition comprising sennosides A, B and A1 which are substantially free from sennosides C, D and D1 and from aloe-emodin components.

14. The composition of claim 13 wherein the composition is a pharmaceutical composition.

15. The pharmaceutical composition of claim 14 further comprising one or more carriers or adjuvants.

* * * * *

UNITED STATES PATENT AND TRADEMARK OFFICE
CERTIFICATE OF CORRECTION

PATENT NO. : 5,710,260
DATED : January 20, 1998
INVENTOR(S) : Alfons CARCASONA et al.

It is certified that error appears in the above-indentified patent and that said Letters Patent is hereby corrected as shown below:

In column 3, line 25, change "PH" to -- pH --.

In column 5, line 21, after "are" delete -- in --.

In column 5, line 50, change "50" to -- 30 --.

In column 8, line 53, after "against" delete "au" and insert therefor -- an --.

In column 9, line 62, after "calcium" delete -- - - - --.

Signed and Sealed this

Ninth Day of November, 1999

Q. TODD DICKINSON

Attest:

Attesting Officer

Acting Commissioner of Patents and Trademarks